United States Patent [19]

Kulpe et al.

[11] Patent Number: 5,292,971
[45] Date of Patent: Mar. 8, 1994

[54] FLOURINE-SUBSTITUTED VICINAL AND METHOD FOR THEIR PREPARATION, AND THEIR USE

[75] Inventors: Jürgen Kulpe; Heinz Strutz, both of Frankfurt am Main, Fed. Rep. of Germany

[73] Assignee: Hoechst Aktiengesellschaft, Frankfurt am Main, Fed. Rep. of Germany

[21] Appl. No.: 17,687

[22] Filed: Feb. 12, 1993

[30] Foreign Application Priority Data

Feb. 29, 1992 [DE] Fed. Rep. of Germany ........ 4206384

[51] Int. Cl.⁵ .............................................. C07C 35/29
[52] U.S. Cl. .................................. 568/819; 568/817; 568/820; 568/821; 568/822
[58] Field of Search ............... 568/817, 818, 821, 815, 568/822, 820, 819

[56] References Cited

U.S. PATENT DOCUMENTS

| | | | |
|---|---|---|---|
| 2,983,732 | 5/1961 | Geering | 568/820 |
| 3,007,958 | 11/1961 | Robitschek et al. | 568/820 |
| 3,255,254 | 6/1966 | Kauer | 568/820 |
| 3,393,993 | 7/1968 | Gilbert et al. | 568/821 |
| 3,419,903 | 12/1968 | Hoch | 568/820 |
| 4,510,025 | 4/1985 | Matsubara et al. | 568/820 |
| 4,562,299 | 12/1985 | Venturello et al. | 568/821 |

*Primary Examiner*—Werren B. Lone

*Attorney, Agent, or Firm*—Connolly and Hutz

[57] ABSTRACT

Fluorine-substituted vicinal glycols of the formula

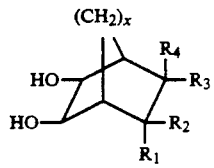

in which the substituents $R_1$ to $R_4$, independently of one another, have the following meanings: $R_1$ to $R_4 = H$, fluorine, $C_1$- to $C_{18}$-alkyl in which some or all of the hydrogens may be substituted by fluorine, and at least one of the substituents $R_1$ to $R_4$ is a completely fluorinated alkyl or an alkyl of the formula $$-(CH_2)_m-(C_nF_{2n+1}),$$

in which m is 1 or 2, and n is an integer from 1 to 17, and x is 0 or 1.

Furthermore, a method for the preparation of the fluorinated vicinal glycols is described. If the fluorinated vicinal glycols are condensed together with dicarboxylic acids, products having enhanced thermal stability are obtained.

8 Claims, No Drawings

FLOURINE-SUBSTITUTED VICINAL AND METHOD FOR THEIR PREPARATION, AND THEIR USE

The present invention relates to fluorine-substituted vicinal glycols of the formula

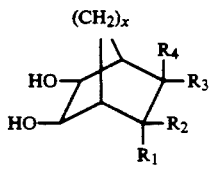

in which the substituents $R_1$ to $R_4$, independently of one another, have the following meanings:

$R_1$ to $R_4$ = H, fluorine, $C_1$- to $C_{18}$-alkyl in which some or all of the hydrogens may be substituted by fluorine, and at least one of the substituents $R_1$ to $R_4$ is a completely fluorinated alkyl or an alkyl of the formula

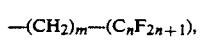

in which m is 1 or 2, and n is an integer from 1 to 17, and x is 0 or 1, a method for their preparation, and their use.

From the wide range of possible fluorine-substituted vicinal glycols, the following compounds are of particular interest:

a) 2,3-dihydroxy-5,5-bis(trifluoromethyl)bicyclo[2.2.1]heptane,

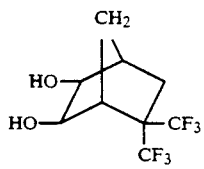

b) 2,3-dihydroxy-5,6,6-trifluoro-5-(trifluoromethyl)-bicyclo[2.2.1]heptane,

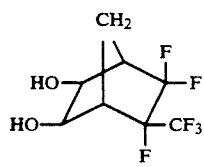

c) 2,3-dihydroxy-5-(perfluorohexyl)bicyclo[2.2.1]heptane,

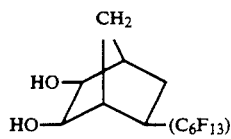

d) 2,3-dihydroxy-5-(perfluorooctyl)bicyclo[2.2.1]heptane,

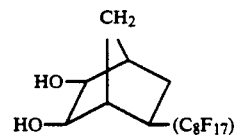

e) 1,2-dihydroxy-4-(perfluorohexyl)cyclohexane,

f) 2,3-dihydroxy-5-(2,2,3,3,4,4,5,5,6,6,7,7,7-tridecafluoroheptyl)bicyclo[2.2.1]heptane,

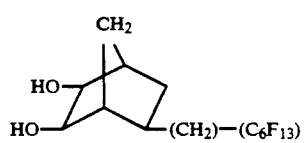

g) 2,3-dihydroxy-5-(3,3,4,4,5,5,6,6,7,7,8,8,8-tridecafluorooctyl)bicyclo[2.2.1]heptane

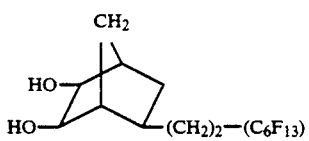

The starting materials for the preparation of fluorine-substituted vicinal glycols are the reaction products of butadiene or cyclopentadiene with a fluorine-substituted alkene. The reaction of butadiene or cyclopentadiene with olefins is described in the literature as a "Diels-Alder reaction". J. Am. Chem. Soc. (1955), Vol. 77, 915–919 and J. Org. Chem. (1973), Vol. 38, No. 11, 2027–2042 describe reactions for the preparation of bicyclo[2.2.1]heptene derivatives which contain fluorine and are suitable as starting materials for the preparation of the fluorine-substituted vicinal glycols.

The method for the preparation of the fluorine-substituted vicinal glycols according to the invention from the reaction product of butadiene or cyclopentadiene with a fluorine-substituted alkene according to the procedure of a Diels-Alder reaction comprises reacting the reaction product with hydrogen peroxide in the presence of an acid at temperatures between 40° and 100° C. and isolating the fluorine-substituted vicinal glycol.

The method for the preparation of the fluorine-substituted vicinal glycols according to the invention can, optionally and preferably, be carried out in such a way that 1) hydrogen peroxide of 30 to 70% strength is used in an amount of 1 equivalent to 5 equivalents of oxidant, based on the Diels-Alder reaction product used, 2) the acid used is formic acid, acetic acid, propionic acid or aqueous sulfuric acid, together with a catalytic amount of $[CH_3N(C_3H_{17})_3][PO_4\{W(O)(O_2)_2\}_4]$, 3) the Diels-Alder reaction product is mixed with a 0.1- to 10-fold amount of acid, 4) the reaction is carried out in sulfuric acid of 1 to 50 percent by weight strength.

5) 0.1 to 10 mol percent of [CH$_3$N(C$_8$H$_{17}$)$_3$][PO$_4$\{W(O)(O$_2$)$_2$\}$_4$]are used, based on the Diels-Alder reaction product, 6) the fluorine-substituted vicinal glycol is purified by a sublimation, 7) the acid-containing fluorine-substituted vicinal glycol is treated with aqueous sodium hydroxide, the aqueous phase is extracted with methylene chloride, the extract is combined with the organic phase and dried, and the methylene chloride is then distilled off.

The fluorine-substituted vicinal glycols according to the invention can be used for the preparation of polyesters by condensing fluorine-substituted vicinal glycols with dicarboxylic acids. These products are notable for enhanced thermal stability. Enhanced thermal stability of polyesters can also be achieved by condensing as little as 5 to 50 mol percent of fluorine-substituted vicinal glycols in a mixture with glycols together with dicarboxylic acids.

The preparation method chosen for the Diels-Alder reaction product results in an isomer mixture of exo- and endo-addition products. However, it is also possible to use the pure exo- or endo-addition products of a Diels-Alder reaction as the starting material for the preparation of fluorine-substituted vicinal glycols.

EXAMPLE A (DIELS-ALDER REACTION)

A 1 l autoclave is charged with 554 ml =864 g (2.5 mol) of perfluorohexylethene, 165 g (2.5 mol) of freshly distilled cyclopentadiene and 5 g of hydroquinone. The autoclave is purged twice with nitrogen. It is then pressurized to 5 bar with nitrogen and heated to 170° C. After 72 hours, the reaction mixture is allowed to cool, the excess nitrogen pressure is vented, and the autoclave contents are filtered into a distillation flask. Fractional distillation under reduced pressure gives 783 g of the Diels-Alder product with a boiling point of 33°-35° C. at a pressure of 0.25 mm Hg. An endo/exo isomer ratio of 77:23 was determined by $^1$H NMR spectroscopy.

The following examples are intended to explain the preparation of the compounds according to the invention.

EXAMPLE 1

Preparation of 2,3-dihydroxy-5,5-bis(trifluoromethyl)bicyclo[2.2.1-]heptane 5.2 g (20 mmol) of the Diels-Alder reaction product of 3,3,3-trifluoro-2-trifluoromethyl-1-propene (hexafluoroisobutene) and cyclopentadiene are mixed with 20 ml of formic acid, and 1.3 ml of 70 percent strength hydrogen peroxide (30 mmol) is added at 50° C., and the mixture is held at 50° C. for 20 hours. Testing for oxidant using KI-starch paper showed that the oxidant had been broken down completely. The low-boiling components are distilled off under reduced pressure. The residue is heated to 50° C. with 200 ml of 20% strength aqueous sodium hydroxide. The precipitated solid is extracted with a total of 130 ml of methylene chloride. The combined extracts are dried with magnesium sulfate, the methylene chloride is distilled off, and the residue is sublimated at 60° C. in an oil pump vacuum.

Yield: 3.28 g =62% of theory.
Melting point: 88°-100° C.

EXAMPLE 2

Preparation of 2,3-dihydroxy-5,6,6-trifluoro-5-(trifluoromethyl)bicyclo[2.2.1]heptane 4.3 g (20 mmol) of the Diels-Alder reaction product of hexafluoropropene and cyclopentadiene are mixed with 10 ml of water, 1 ml of 30 percent strength sulfuric acid and 400 mg of the catalyst [CH$_3$N(C$_8$H$_{17}$)$_3$][PO$_4$\{W(O)(O$_2$)$_2$\}$_4$]whose preparation is described in Synthesis 296 (1989), and the mixture is heated to 60° C. 1.7 ml (40 mmol) of 70 percent strength hydrogen peroxide is then added, and the emulsion is kept at 60° C. for 6 hours. Upon cooling, a white solid precipitates which is filtered off with suction and washed with cold water. The crude product is then purified by sublimation at a pressure of 0.1 mbar and a temperature of 50 ° C.

Yield: 4.75 g =94% of theory.

EXAMPLE 3 a

Preparation of 2,3-dihydroxy-5-(perfluorohexyl)bicyclo[2.2.1]heptane 8.2 g (20 mmol) of the Diels-Alder reaction product of 3,3,4,4,5,5,6,6,7,7,8,8,8-tridecafluoro-1-octene (perfluorohexylethene) and cyclopentadiene are mixed with 20 ml of formic acid, 1.3 ml of 70 percent strength hydrogen peroxide (30 mmol) is added at 60° C., and the mixture is held at 60° C. for 36 hours. The low-boiling components are distilled off in vacuo. The residue is extracted with three portions (130 ml in total) of methylene chloride. The combined extracts are dried with magnesium sulfate and the methylene chloride is removed in vacuo. The residue is sublimed at 95° C. in an oil pump vacuum.

Yield: 3.83 g =43% of theory.

EXAMPLE 3 b

Preparation of 2,3-dihydroxy-5-(perfluorohexyl)bicyclo2.2.1]heptane 82.4 g (200 mmol) of the Diels-Alder reaction product of 3,3,4,4,5,5,6,6,7,7,8,8,8-tridecafluoro-1-octene (perfluorohexylethene) and cyclopentadiene are mixed with 20 ml of water, 10 ml of 30 percent strength sulfuric acid and 2 g of [CH$_3$N(C$_8$H$_{17}$)$_3$][PO$_4$\{W(O)(O$_2$)$_2$\}$_4$], and 2 ml of a total of 34.4 ml (200 mmol) of 35 percent strength hydrogen peroxide are added, and the mixture is heated to 60° C. while stirring. At this temperature the remaining hydrogen peroxide is added dropwise within 30 minutes. As the reaction progresses, the suspension becomes increasingly more viscous. After 17 hours, the organic phase is separated off as the bottom phase of the reaction mixture, the aqueous phase is extracted with 200 ml of methylene chloride, and the combined organic phases are dried with sodium sulfate. As the solvent is distilled off, a white solid precipitates which is washed with heptane at 0° C.

Yield: 83.9 g =94% of theory.

EXAMPLE 4

Preparation of 2,3-dihydroxy-5-(perfluorooctyl)bicyclo2.2.1]heptane 10.2 g (20 mmol) of the Diels-Alder reaction product of 3,3,4,4,5,5,6,6,7,7,8,8,9,9,10,10,10-heptadecafluoro-1-decene (perfluorooctylethene) and cyclopentadiene are mixed with 20 ml of formic acid, 2.6 ml of 35 percent strength hydrogen peroxide (30 mmol) are added at a temperature of 50° C., and the mixture is held at 50° C. for 36 hours. The solvent is stripped off in vacuo, and the residue is heated to 50° C. with 100 ml of 4% strength aqueous sodium hydroxide. Two phases form during this process. After neutralization with hydrochloric acid, the aqueous phase is extracted with 3 portions (200 ml in total) of methylene chloride. The extracts and the organic phase are combined and dried with sodium sulfate. The methylene chloride is then removed in vacuo. The residue is sublimed at 112° C. in an oil pump vacuum.

Yield: 4.54 g =43% of theory.

EXAMPLE 5

Preparation of 2,3-dihydroxy-5-(2,2,3,3,4,4,5,5,6,6,7,7,7-tridecafluoroheptyl)bicyclo[2.2.1]heptane 4.3 g (10 mmol) of the Diels-Alder reaction product of 4,4,5,5,6,6,7,7,8,8,9,9,9-tridecafluoro-1-nonene (perfluorohexyl-propene-1) and cyclopentadiene are mixed with 10 ml of water, 1 ml of 30 percent strength sulfuric acid and 200 g of $[CH_3N(C_8H_{17})_3][PO_4\{W(O)(O_2)_2\}_4]$, 1.7 ml (20 mmol) of 35 percent strength hydrogen peroxide is added, and the mixture is heated to 60° C. while stirring. As the reaction progresses, the emulsion becomes increasingly more viscous. After 17 hours, the mixture is cooled and the precipitated white solid is taken up in methylene chloride. The solution obtained is washed twice with water and dried with sodium sulfate. The solvent is removed under reduced pressure, and the residue is sublimed at 100° C. and 0.1 mbar.

Yield: 2.6 g =55% of theory.

We claim:

1. A fluorine-substituted vicinal glycol of the formula

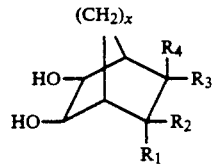

in which $R_1$ is an alkyl of the formula $$-(CH_2)_m-(C_nF_{2n+1}),$$

in which m is 1 or 2, and n is an integer from 1 to 17, and x is 0 or 1 and $R_2$, $R_3$ and $R_4$ are the same or different and are radicals selected from the group consisting of H, fluorine, $C_1$ to $C_{18}$-alkyl, fluorine-substituted $C_1$ $C_{18}$-alkyl and an alkyl of the formula $$-(CH_2)_m-(C_nF_{2n+1}),$$

in which m is 1 or 2, and n is an integer from 1 to 17.

2. A fluorine-substituted vicinal glycol consisting of 2,3-dihydroxy-5,5-bis(trifluoromethyl)bicyclo[2.2.1]heptane.

3. A fluorine-substituted vicinal glycol consisting of 2,3-dihydroxy-5,6,6-trifluoro-5-(trifluoromethyl)-bicyclo[2.2.1]heptane.

4. A fluorine-substituted vicinal glycol consisting of 2,3-dihydroxy-5-(perfluorohexyl)-bicyclo[2.2.1]-heptane.

5. A fluorine-substituted vicinal glycol consisting of 2,3-dihydroxy-5-(perfluorooctyl)-bicyclo[2.2.1]-heptane.

6. A fluorine-substituted vicinal glycol consisting of 1,2-dihydroxy-4-(perfluorohexyl)cyclohexane.

7. A fluorine-substituted vicinal glycol consisting of 2,3-dihydroxy-5-(2,2,3,3,4,4,5,5,6,6,7,7,7-tridecafluoroheptyl)bicyclo[2.2.1]heptane.

8. A fluorine-substituted vicinal glycol consisting of 2,3-dihydroxy-5-(3,3,4,4,5,5,6,6,7,7,8,8,8-tridecafluorooctyl)bicyclo[2.2.1]heptane.

* * * * *